United States Patent [19]

Oepen et al.

[11] 4,435,563
[45] Mar. 6, 1984

[54] PROCESS FOR THE RECOVERY OF PURE HELLEBRIN

[75] Inventors: Gerhard Oepen, Maintal; Karl-Heinz Mangartz, Kahl; Norbert Seifried, Hanau; Jürgen Engel, Alzenua; Otto Isaac, Hanau, all of Fed. Rep. of Germany

[73] Assignee: Degussa Aktiengesellschaft, Frankfurt, Fed. Rep. of Germany

[21] Appl. No.: 377,251

[22] Filed: May 11, 1982

[51] Int. Cl.$^3$ .............................................. C07J 19/00
[52] U.S. Cl. .................................. 536/18.1; 536/127; 536/128; 536/185
[58] Field of Search ..................... 536/18.1, 128, 127, 536/18.5

[56] References Cited

U.S. PATENT DOCUMENTS 3,904,598 9/1975 Isaac .................................. 536/18.1
3,912,716 10/1975 Isaac .................................. 536/18.1

FOREIGN PATENT DOCUMENTS 101577 12/1959 Czechoslovakia .
605073 11/1934 Fed. Rep. of Germany .
2038110 2/1972 Fed. Rep. of Germany .
2123535 11/1972 Fed. Rep. of Germany .

OTHER PUBLICATIONS

Tschesche, Z. Naturforschg. 20b, 707 (1963).
Petricic, Acta Pharm., Jug. 17, 29 (1969).
Chem. Abst. vol. 67, p. 5400, item 57272c (1967).
Karrer, Helv. Chimica Acta, vol. 26 (1943) pp. 1353–1363.

*Primary Examiner*—Johnnie R. Brown
*Assistant Examiner*—Elli Peselev
*Attorney, Agent, or Firm*—Cushman, Darby & Cushman

[57] ABSTRACT

There is provided a process for the recovery of pure hellebrin which comprises extracting a defatted hellebrin extract dissolved in a water-alkanol mixture or water-acetone mixture with a mixture of a lower alkanol or acetone and di-, tri-, or tetrachloromethane (or dichloroethane) evaporating the extraction agent in a vacuum and then heating with ethanol until the deposition of the first hellebrin crystals begins.

10 Claims, 2 Drawing Figures

PROCESS FOR THE RECOVERY OF PURE HELLEBRIN

BACKGROUND OF THE INVENTION

The heart active glycoside hellebrin is contained in the roots of the Helleborus species. It is of increased therapeutic interest because of its intermediate position between Stropanthus and *Scilla glycosides.*

It is known that a glycoside acting in a manner similar to digitalis can be recovered from Helleborus niger by treating aqueous Helleborus with carbon, the carbon adsorbate extracted with organic solvents and the extract obtained subjected to a further purification (German Pat. No. 605,073). The carbon treatment can also precede a lead precipitation wherein the excess lead is removed with phosphate (Helv. Chim. Acta 26, 1353 (1943) or with sulfate (Farmacia (Bucharest) P 407 (1959). This process is not satisfactory.

The disadvantages of the adsorptive precipitation are avoided according to a new process if Helleborus extract is treated successively with different solvents (Czechoslovakian Pat. No. 101,577). This process, however, not only requires a large expenditure of solvents but reworking has shown that as a rule the process does not lead to crystallizable hellebrin.

There has also been described a chromatographic purification of Helleborus extract on aluminum oxide in combination with a preceding lead precipitation (Med. prom. SSR 18, 12 (1964) or without such pretreatment (Planta med. 9, 64 (1961)). The yield of hellebrin, however, only amounts to 0.04%.

More favorable yields are obtained by chromatography or silica gel (Z. Naturforschg. 20b, 707(1965); Acta Pharm. Jug. 17, 29 (1967)). In the previously used silica gels, however, it is a matter of using finely divided silica gels (particle size 0.01 to 0.04 mm, which only permit moderate speeds. Also the capacity of silica gel columns generally is only half as much as that of alumina columns of equal size. Thus this method of separation up to now has been suited only for the recovery of small amounts of hellebrin.

Newer processes operate with a coarse particle silica gel having a particle size of 0.15 to 10 mm (German Pat. Nos. 2,038,110 and 2,123,535 and related Isaac U.S. Pat. No. 3,904,598 and Isaac U.S. Pat. No. 3,912,716. The entire disclosure of the two Isaac U.S. patents is hereby incorporated by reference and relied upon.). In this case there is employed an extract, which for example had been obtained by extraction of a hellebrin containing drug with chloroform-ethanol (2:1 by volume), whereby a very large amount of this extraction agent is required and this extraction furthermore is very long, for example 5 days.

SUMMARY OF THE INVENTION

There is provided a process for the recovery of pure hellebrin which comprises extracting a defatted hellebrin extract dissolved in a water-alkanol mixture or water-acetone mixture with a mixture of a lower alkanol or acetone and di, tri- or tetrachloromethane (or dichloroethane), evaporating the extraction agent in a vacuum and then heating with ethanol until the deposition of the first hellebrin crystals begins.

Through the process of the invention it is possible to reduce the consumption of organic solvent in the extract and the previously large expenditure of time and besides to eliminate the chromatographic step always necessary previously for the production of pure hellebrin, which step likewise is associated with considerable expenditure of material and time.

To carry out the process of the invention a hellebrin containing extract in a water -$C_1$-$C_3$ alkanol mixture or in a water-acetone mixture is subjected to a liquid-liquid extraction with a halohydrocarbon -$C_1$-$C_3$-alkanol mixture or a halohydrocarbon-acetone mixture.

As chlorohydrocarbons there is employed methylene chloride, chloroform, or carbon tetrachloride, 1,1-dichlorethane or 1,2-dichlorethane.

The water -$C_1$-$C_3$-alkanol mixture or the water-acetone mixture in which the hellebrin containing extract is present for the further extraction contains 20–40 parts by volume, preferably 25–30 parts by volume of the $C_1$-$C_3$-alkanol or acetone based on 100 parts by volume total of alkanol or acetone and halohydrocarbon. The $C_1$-$C_3$-alkanol can also be present in the stated proportion in the form of a mixture of different $C_1$-$C_3$-alkanols. In case the hellebrin extract was obtained by extraction of the drug with other solvents these are removed in a vacuum and the hellebrin containing residue dissolved in the water -$C_1$-$C_3$-alkanol mixture or a water-acetone mixture. As $C_1$-$C_3$-alkanols there are particularly considered methanol, ethanol, propanol and isopropanol, preferably ethanol.

The content of hellebrin in the water -$C_1$-$C_3$-alkanol mixture or water-acetone mixture should be 2–20 mg of hellebrin, preferably 4–10 mg of hellebrin per 1 gram of extract solution.

As extraction liquid there is used a mixture of di-, tri-, tetrachloromethane or dichlorethane and $C_1$-$C_3$-alkanol (or acetone). In this mixture the portion of $C_1$-$C_3$-alkanol (or acetone) can be between 15–35 volume percent, especially 20–30 volume percent. The portion of halohydrocarbon is between 85–65 volume percent, especially 70–80 volume percent, for example at 75 volume percent. The mixture can consist of an individual alkanol and of an individual halohydrocarbon mentioned or it can consist of a mixture of alkanols and a mixture of di-, tri-, and tetrachloromethane and dichlorethane or a mixture of only three or two of the halohydrocarbons mentioned. Likewise acetone can be used with one of the halohydrocarbons or a mixture of the halohydrocarbons. As $C_1$-$C_3$-alkanols there can be employed those already mentioned. Preferably there is employed as extraction liquid a mixture of chloroform/ethanol or a methylene chloride/ethanol, carbon tetrachloride/ethanol, 1,1-dichloroethane/ethanol, or 1,2-dichoroethane/ethanol (halohydrocarbon/ethanol—6-5–75 volume percent: 35–25 volume percent).

As hellebrin containing starting materials there may be especially considered the roots of Helleborus niger but there can also be used roots from other Helleborus sources, for example *Helleborus foetidus, Helleborus multifidus, Helleborus odorus Helleborus orientalis, Helleborus purpurascens, Helleborus viridis.*

The extraction itself can be carried out in the customary extraction apparatuses for this purpose, in which case these can be operated continuously or semi-continuously. Preferably there are used extraction apparatuses which operate in countercurrent processes as for example, unpulsated perforated plate column having horizontal or vertical perforated plates or Mixer-Settler apparatuses.

In case an unpulsated perforated plate column is used, this is fixed by the following characteristics:

1. Average Load

The average loads of the organic phase and aqueous phase can be between 5–20 m$^3$/(m$^2$×h), in which case the average loads for the organic phase (the halohydrocarbon phase) and the aqueous phase preferably are equal. The feed ratio, which is defined as the quotient from the average load of the aqueous phase/average load of the halohydrocarbon phase, can generally have values from 1.5:1 to 1:1.5, preferably it has the value 1:1.

2. The number of plates for the perforated plate column can be between 20 and 40, preferably 30. The distance of the plates from each other can be between 100–250 mm, preferably 150 mm.

The height of the column portion which contains the perforated plates is 3–6 meters, preferably 4 meters; the height of the head of the column is 0.3–1 meter, preferably 0.5 meter; the height of the column sump is 0.3–1 meter, preferably 0.5 meter.

3. Perforated Plates

Basically the perforated plates can be made of the materials usually employed for this purpose, preferably there are used synthetic resin perforated plates or perforated plates coated with synthetic resin, in which case the synthetic resin is especially Teflon (polytetrafluoroethylene or perfluoroethylene-perfluoropropylene copolymer) or polypropylene.

The free hole area (the sume of all the hole areas of a perforated plate based on the total areas of the perforated plates) is 1–4%, preferably 1.5–2.5%. Hereby the free hole area should decrease from the bottom, that is from the sump of the column upwardly, that is up to the last plate in the head of the column. This decrease of the hole area of the plate can take place steadily or also stepwise (for example in 3, 4, or more steps).

If for example, the free hole area of the lowermost plate is in the range between 4–2.5%, then there takes place suitably a decrease of the free hole area up to the last plate to the range between 1.5–1%.

Preferably the free hole area of the lowermost plate is 2.5%, in which case then for example, the free hole area should decrease to 1.5% (that is the last plate in the head of the column has a free hole area of 1.5%). The hole diameters are 1.5–3 mm, preferably 2 mm.

Each perforated plate contains a discharge pipe for the halohydrocarbon phase (heavy phase). The length of this discharge pipe for each plate is the same, for example between 80 and 230 mm, preferably 120 mm. The cross-sectional area of the discharge tube is between 3 and 15% of the cross-sectional area of the column, preferably 4–8%.

The average residence time of the phases in the extraction column for an unpulsated perforated plate column for the single passage is, for example, 0.5–1.5 hours.

In using a Mixer-Settler apparatus this is preferably operated in several stages, in which case the phases participating in the extraction then flow in countercurrent through the entire apparatus. However, there also is the possibility of acting on any of these stages with fresh solvent (cross-current). Suitably there is used a two to six stage, especially a four-stage Mixer-Settler apparatus. The average residence time in the Mixer-Settler apparatus for example is between 0.5–15 hours, especially 3 hours.

The equal phase ratio of organic (heavy) phase to aqueous (light) phase is just as true for the Mixer-Settler apparatus as for the unpulsated perforated plate, that is the ratio of heavy phase to light phase generally is between 1.5:1 to 1:1.5, preferably 1:1.

As starting material there can be used a hellebrin containing drug extract obtained in usual manner. Preferably there is used a hellebrin extract which has been obtained through extraction of a hellebrin containing drug with a mixture of a $C_1$–$C_8$-alkanol (i.e. methanol to octanol) and water preferably methanol-water, ethanol-water, propanol-water, isopropanol-water or butanol-water at a temperature between 50° and 200° C., especially 60°–80° C. The mixing proportion of the alcohol-water-mixture for example, is 4–12 parts by volume of $C_1$–$C_8$-alkanol and 1 part by volume water, especially 9 parts by volume alkanol to one part by volume water. The time of extraction hereby is generally between 2–40 hours especially 5–8 hours. The alcohol-water-extraction agent can then be removed in customary manner in a vacuum. However, it is also possible to employ the aqueous alcoholic extract directly for the further operations, for example, the subsequent defatting. The hellebrin containing drug extract employed is preferably defatted before use of the hellebrin isolation according to the invention. Thus defatting takes place by treating the hellebrin containing drug extract (in solid or syrupy form, that is without solvent, or in solution, for example in an alkanol-water solution) with a mixture of water and hydrocarbons at a temperature between 20°–100° C. for 2–40 hours. Individually for the defatting there are considered for example the following agents: mixture of water and $C_5$–$C_{10}$ alkanes (e.g. pentane, hexane, octane, nonane, decane, isodecane) in the ratio by volume of 2:1, mixtures of water and $C_5$–$C_7$-cycloalkanes (e.g. cyclopentane, cyclohexane, methyl cyclohexane, cycloheptane) and water in the ratio by volume of 2:1, mixtures of water and aromatic hydrocarbons (for example benzene, toluene, xylene) in the ratio by volume of 2:1, mixtures of water and liquid $C_1$–$C_2$-chlorohydrocarbons (for example $CH_2Cl_2$, $CHCl_3$, $CCl_4$, 1,2-dichloroethane) in the ratio by volume of 2:1.

Figure 1:
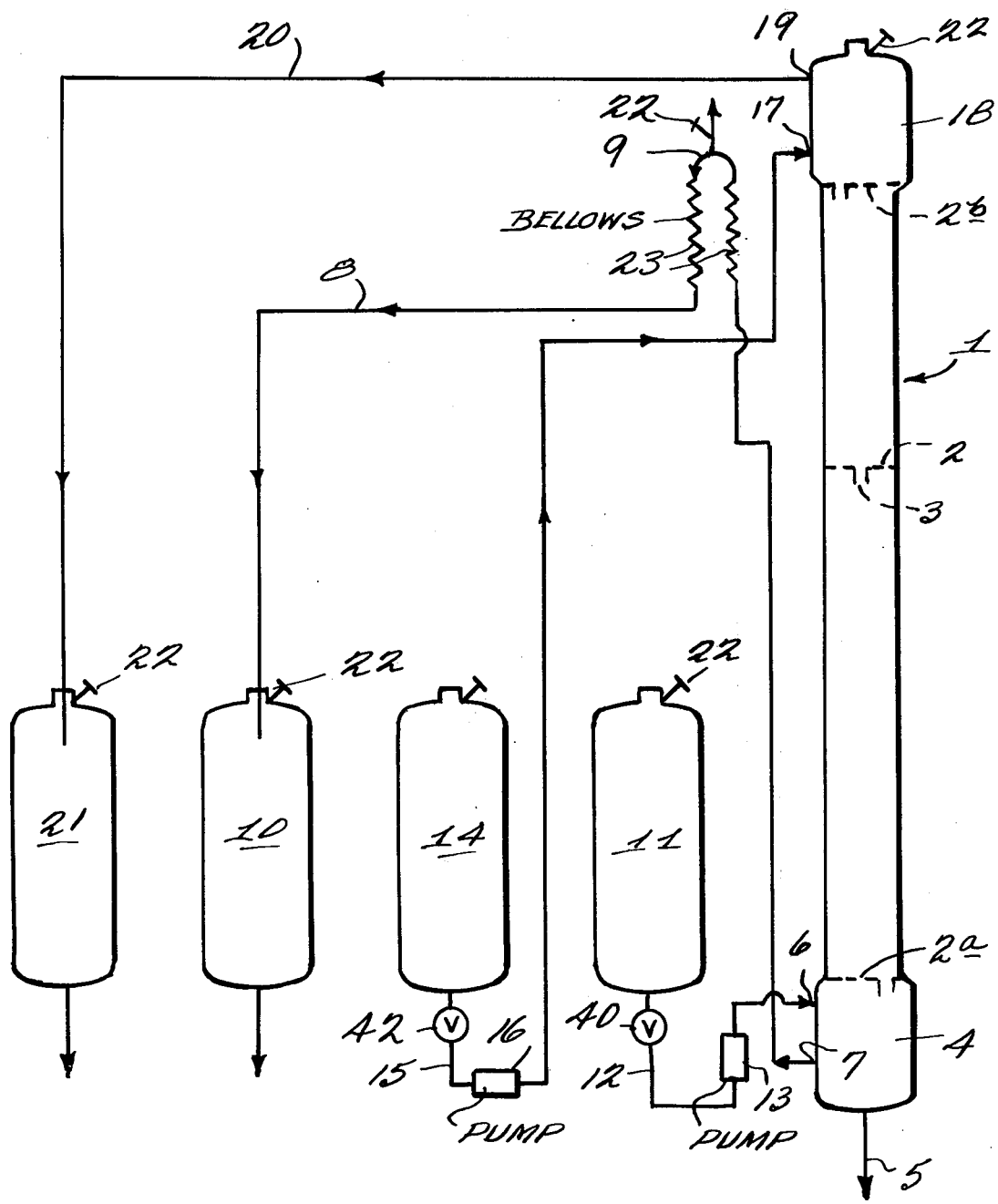
FIG. 1 illustrate the process of the invention employing an unpulsated perforated plate columm.

The process can comprise, consist essentially of, or consist of the stated steps with the recited materials.

DETAILED DESCRIPTION

The process of the invention will be described first in connection with FIG. 1 employing an unpulsating perforated plate column:

The extract to be extracted which is in the water-alcohol mixture or water-acetone mixture is designated as the light phase. The extraction agent which contains essentially halohydrocarbon is designated as the heavy phase.

The column 1 contains the perforated plates 2 (lowest perforated plate 2a, uppermost perforated plate 2b) with the discharge pipes 3 associated therewith in each case. The part of the column below the first perforated plate 2a is the column sump 4 having the discharge line 5, the inlet 6 for the light phase and the outlet 7 for the heavy phase. The outlet 7 for the most part is below the inlet 6, generally 20–50 cm, preferably 30 cm, below the inlet line 6. The inlet 6 is generally located 5–50 cm, preferably 20 cm, below the first perforated plate 2a. The heavy phase flows through the tubular line 8 having the overflow 9 into the collecting vessel 10 for the heavy phase which now contains the hellebrin. The light phase to be extracted is located in the supply vessel 11 and is pumped via valve 40 through tubular line 12 by means of the pump 13 and through the inlet 6 into the sump of the column. The fresh heavy phase, which still contains no extraction material is located in supply vessel 14 and is pumped via valve 42 through tubular line 15 by means of the pump 16 through the inlet 17 into the head of column 18. In the upper part of the column head 18 is located the outlet 19 for the extracted light phase which flows back through the tubular line 20 into the container 21. The openings 22 serve for the release to the air. The tubular line 8 is adjustable upwardly and downwardly so that through this the overflow 9 can be adjusted upwardly. This is important therefore because the adjustment of the separatory layer between lighter and heavier phases in the head of the column can be regulated by the height of the overflow 9. This separatory layer should preferably form in the head of the column 18. This is then the case if the overflow 9 is above the separatory layer light phase/heavy phase but below the outlet 19 (for the light phase). In the case where the heavy phase consists of a mixture of 75 parts by volume of chloroform and 25 parts by volume of ethanol and the separatory layer light phase/heavy phase should be in the middle region of the head of the column 18, the overflow 9 is adjusted to a height which for example, is 10-20 cm, preferably 15 cm, above the separatory layer. If the heavy phase is heavier than given above (for example, it contains more chloroform and/or a heavier halohydrocarbon) then the distance between overflow 9 and the separatory layer is chosen to be less, for example, 2-10 cm, preferably 5 cm. In the converse case, thus if the heavy phase contains less chloroform than is given above and/or contains a lighter halohydrocarbon, then the distance between overflow 9 and the separatory layer is chosen to be larger, for example, 20-30 cm, preferably 25 cm.

Before the beginning of the extraction the column 1 including the column sump is filled with the heavy phase from the supply container 14 via the inlet 17. During the extraction the heavy phase merely stands under the static pressure which is given by the height of the inlet 17. Now the light phase is pumped in through the inlet 6 into the column pump under a slight excess pressure, for example, with a conveying pressure between 0.5-1 bar, preferably 0.8 bar. The light phase rises now in the form of dispersed drops because of its lower specific gravity through the holes of the perforated plates in countercurrent flow to the heavy phase and thereby gives up hellebrin and ethanol to the heavy phase which flows off through the outlet pipe of the individual perforated plates and finally through the outlet 7.

It goes without saying that there also are possible in FIG. 1 other arrangements of the containers 10, 11, 14, and 21 for the light and heavy phases. For example, the container which contains the extraction liquid can be placed at the same height as the inlet 17, then for example, there can be eliminated the pump for conveying the heavy phase through the inlet 17 into the column. Likewise for example, the container 11 with the light phase to be extracted can be placed higher, through which in a given case, likewise there can be eliminated the pump for conveying this phase into the column through the inlet 7.

Already, in a single passage of the light and heavy phases through the column there is obtained according to the working up given in Example 1 300 grams of pure hellebrin (26% yield).

A still higher yield of pure hellebrin is obtained if the light phase flowing back after the first extraction is extracted with the same amount of fresh heavy phase exactly as in the first passage a second time. It is further recommended that the light phase flowing back after the second passage be extracted still a third time with the same amount of fresh heavy phase, through which about 81% of the hellebrin present in the original extract can be obtained.

Figure 2:
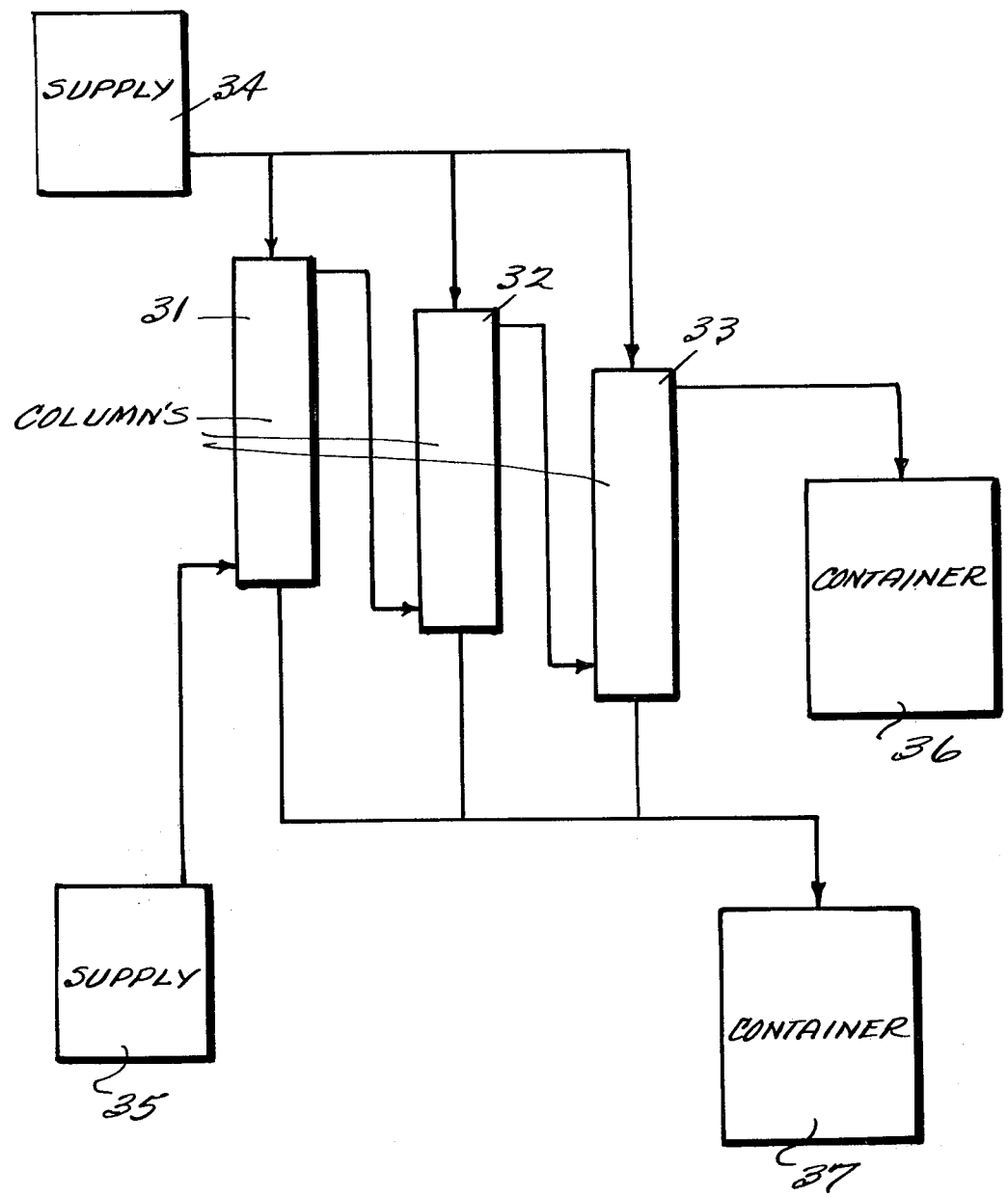
FIG. 2 illustrates a fully continuous process according to the invention.

It should be understood that the process of the invention can also be operated fully continuously, for example by three unpulsated perforated plate columns with the already described characteristic data connected in succession (see FIG. 2). Hereby then in fully continuous operation the containers 11 and 14 of FIG. 1 are constantly correspondingly filled up. However, it is also possible for example to proceed in such manner that only one perforated plate column is used, in which case then the light phase flowing off, in a given case after partial concentration, is treated with new hellebrin extract and in a given case the correct starting ratio of alkanol or acetone to water established by addition of $C_1$-$C_3$ or $C_1$-$C_4$ alkanols and/or acetone and feeding it continuously into the column. Analogously there can be used two columns.

In FIG. 2 the columns 31-33 indicate the perforated plate column 31, the perforated plate column 32 and the perforated plate column 33. The supply of the heavy phase takes place from the supply container 34, the supply of the aqueous hellebrin solution from the supply container 35. The aqueous phase after passing through the columns 31-33 discharges into the container 36, the heavy phase is collected in the container 37.

Example 38 kg of defatted drug extract (hellebrin content: 30.2 mg/g of extract) were diluted to 200 liters of water/ethanol (70:30 parts by volume) and in an unpulsated perforated plate column subjected three times to an exhaustive liquid-liquid-extraction, each time with 200 liters of chloroform/ethanol (75:25 parts by volume) (equal phase ratio of light phase to heavy phase, that is the same average load for light and heavy phases).

The perforated plate column used having horizontal perforated surfaces has the following data:

| | |
|---|---|
| Column diameter: | 50 mm |
| Column height (total) | 5.5 m |
| Number of plates: | 30 (material Teflon) |
| Hole diameter of the perforated plate: | 2 mm |
| Number of holes in the perforated plates: | in plates 1-8: 16 holes |
| | in plates 9-16: 13 holes |
| | in plates 17-24: 10 holes |
| Distance between plates: | 150 mm |
| Length of the outlet pipes belonging to the individual plates: | 120 mm |
| Inner diameter of the outlet pipe: | 10 mm. |

The column was filled with the extraction liquid chloroform-ethanol (heavy phase) from the head of the column; then the hellebrin containing water-ethanol-solution (light phase) was pumped into the upper part of the column sump under a conveying pressure of 1.7 bar (amount conveyed = throughput 12.5 liter/hour). The separatory layer light phase/heavy phase is in the middle section of the column head about 30 cm below the upper edge of the column. The overflow of the heavy phase is about 20 cm below the upper edge of the column. After the entire 200 liters of water-ethanol-extraction solution has passed through the column from the bottom upwardly, this solution is extracted in the same manner with a further 200 liters of fresh chloroform-ethanol-mixture as the heavy phase and subsequently again with the same amount of chloroform-ethanol-mixture. Consequently there were obtained altogether around 600 liters of extraction phase (heavy phase). The 200 liters of heavy phase obtained after the first extraction contained about 300 grams of the water-ethanol-extract containing hellebrin; this 200 liters for example consists of 69 parts by volume of chloroform and 26 parts by volume of ethanol and about 5 volume percent of water. The 200 liters of heavy phase (69 parts by volume of chloroform and 26 parts by volume of ethanol and about 5 volume percent of water) obtained after the second extraction contained about 300 grams and the 200 liters of heavy phase (69 parts by volume of chloroform and 26 parts by volume of ethanol and about 5 volume percent of water) obtained after the third extraction contained again about 300 grams of the hellebrin contained in the original water-ethanol extract. The three extractions were carried out at room temperature. The total extraction time for these three extractions was about 50 hours.

The heavy phase obtained was then concentrated in a vacuum (200 mbar); the solution of about 55 parts by volume chloroform and 45 parts by volume of ethanol resulting hereby can, in a given case, after addition of chloroform or ethanol for adjusting the mixing ratio used, be used again for new extractions.

The syrupy residue (7.5 kg) obtained was then treated with 8 liters of ethanol and the total heated under reflux until the entire residue was dissolved and the first hellebrin crystals began to separate (about 3–4 hours). In the cooling the hellebrin precipitates in the form of a finely crystalline precipitate. The hellebrin was filtered with suction and then washed three times with ethanol.

Yield of Crystalline hellebrin: 70% (720 grams).

The drug extract used as starting material was obtained as follows:

20 kg of dry, ground drug (particle size 1–3 mm) is heated in a 240 liter V$_2$A steel apparatus (important = bottom cleanout ball valve having a diameter of at least 100 mm) with a mixture of 135 liters of methanol and 15 liters of water (ratio methanol/water = 9:1) for 6 hours under stirring and reflux (thereby there can occur strong foam formation). After cooling to about 50° C. the mixture is discharged with continuous stirring and immediately centrifuged. After washing the residue with 10 liters of methanol the extraction solution is concentrated in a rotary evaporator to about 15 liters.

The degree of extraction is 92% (418 grams of hellebrin).

Defatting the Drug Extract:

15 kg of the precedingly described concentrated extract is treated with 15 liters of water and stirred intensively for 1 hour. Then there is added 7.5 liters of methylene chloride and stirring continued for a further 2 hours. For phase separation the mixture is then allowed to rest for 16–20 hours. The lower, organic phase contains waxes and fats. Together with a tarry intermediate layer it is discarded or concentrated for the recovery of the dichloromethane. The aqueous phase contains the desired crude hellebrin, besides other materials, and is concentrated to about 50% dry material.

What is claimed is:

1. A process for the recovery of pure hellebrin by extraction of a defatted hellebrin extract and deposition of the pure hellebrin by heating the extraction residue in the presence of ethanol comprising multistep countercurrent extracting a defatted hellebrin containing extract in a solvent which is a water -$C_1$-$C_3$-alkanol mixture or a water-acetone mixture with a solvent mixture consisting of a $C_1$-$C_3$-alkanol or acetone and a chlorohydrocarbon which is dichloromethane, trichloromethane, tetrachloromethane or dichloroethane and subsequently concentrating the hellebrin containing chloromethane or chloroethane phase in a vacuum and heating the thus obtained syrupy residue in ethanol under reflux until the residue is dissolved completely and the first hellebrin crystals begin to deposit.

2. A process according to claim 1 wherein the defatted hellebrin extract is in a solvent which is a water -$C_1$-$C_3$-alkanol mixture or a water-acetone mixture and the extraction is carried out with a solvent mixture consisting of a $C_1$-$C_3$-alkanol or acetone and dichloromethane, trichloromethane or tetrachloroethane.

3. A process according to claim 2 wherein the defatted hellebrin extract is in a solvent which is a water -$C_1$-$C_3$-alkanol mixture and the extraction is carried out with a solvent mixture consisting of a $C_1$-$C_3$-alkanol and dichloromethane, trichloromethane or tetrachloromethane.

4. A process according to claim 3 wherein the defatted hellebrin extract is a water-ethanol mixture and the extraction is carried out with a mixture of ethanol and trichloromethane.

5. A process according to claim 1 wherein the defatted hellebrin extract is in a solvent mixture which contains 20–40 parts by volume of the $C_1$-$C_3$-alkanol or acetone and 80–60 parts by volume of water and the extraction is carried out with a solvent mixture which contains 15–35 parts by volume of the $C_1$-$C_3$-alkanol or acetone and 85–65 parts by volume of the halohydrocarbon.

6. A process according to claim 2 wherein the defatted hellebrin extract is in a solvent mixture which contains 20–40 parts by volume of the $C_1$-$C_3$-alkanol or acetone and 80–60 parts by volume of water and the extraction is carried out with a solvent mixture which contains 15–35 parts by volume of the $C_1$-$C_3$-alkanol or acetone and 85–65 parts by volume of the halohydrocarbon.

7. A process according to claim 3 wherein the defatted hellebrin extract is in a solvent mixture which contains 20–40 parts by volume of the $C_1$-$C_3$-alkanol and 80–60 parts by volume of water and the extraction is carried out with a solvent which contains 15–35 parts by volume of $C_1$-$C_3$-alkanol and 85–65 parts by volume of the halohydrocarbon.

8. A process according to claim 7 wherein the $C_1$-$C_3$-alkanol is ethanol and the halohydrocarbon is trichloromethane.

9. A process according to claim 1 comprising carrying out the extraction in a perforated plate column or in a mixer-settler apparatus.

10. A process according to claim 9 comprising carrying out the extraction in a perforated plated column.

* * * * *